(12) United States Patent
Wei et al.

(10) Patent No.: US 7,806,968 B2
(45) Date of Patent: Oct. 5, 2010

(54) CALIBRATION UNIT FOR VOLATILE PARTICLE REMOVER

(75) Inventors: Qiang Wei, Novi, MI (US); Montajir M D. Rahman, Hayes (GB); Michael Akard, Ann Arbor, MI (US)

(73) Assignee: Horiba Ltd., Kyoto (JP)

( * ) Notice: Subject to any disclaimer, the term of this patent is extended or adjusted under 35 U.S.C. 154(b) by 215 days.

(21) Appl. No.: 11/872,961

(22) Filed: Oct. 16, 2007

(65) Prior Publication Data

US 2009/0094950 A1    Apr. 16, 2009

(51) Int. Cl.
*B03C 3/68* (2006.01)
(52) U.S. Cl. .................... 96/18; 95/1; 55/419; 73/1.04; 73/1.16; 73/23.2; 73/861.41; 73/863.03; 239/71
(58) Field of Classification Search .................. 95/1; 55/419; 73/1.04, 1.05, 1.16, 23.2, 23.31, 73/861.41, 863.03, 863.23, 865.5; 239/71
See application file for complete search history.

(56) References Cited

U.S. PATENT DOCUMENTS

| 5,712,433 | A | * | 1/1998 | Kojima .................... 73/863.03 |
| 6,263,744 | B1 | | 7/2001 | Russell et al. |
| 6,405,577 | B2 | * | 6/2002 | Hanashiro et al. .......... 73/23.31 |
| 6,439,027 | B1 | | 8/2002 | Hiss, III |
| 2006/0179960 | A1 | | 8/2006 | Wei |
| 2007/0028662 | A1 | | 2/2007 | Wei et al. |

OTHER PUBLICATIONS

Qiang Wei, Karl Oestergaard, Scott Porter, Asano Ichiro, Masayuki Adachi, Rahman M. Montajir, Real-Time Measuring System for Engine Exhaust Solid Particle Number Emission—Design and Performance, SAE 2006-01-0864, SAE International, 2006.
Qiang Wei, Asano Ichiro, Masayuki Adachi, Rahman M. Montajir, Takeshi Kusaka, Yuichi Goto, Real-Time Measuring System for Engine Exhaust Solid Particle Number Emission—Performance and Vehicle Tests, SAE 2006-01-0865, SAE International, 2006.
Conclusions on improving particulate mass measurement procedures and new particle number measurement procedures relative to the requirements of the 05 series of amendments to regulation No. 83, GRPE-48-11-Rev 1, 48th GR PE, Jun. 1-4, 2004, agenda item 2, 2004.

* cited by examiner

*Primary Examiner*—Robert J Hill, Jr.
*Assistant Examiner*—Christopher P Jones
(74) *Attorney, Agent, or Firm*—Brooks Kushman P.C.

(57) ABSTRACT

A penetration and removal efficiency calibration unit for a volatile particle remover in a solid particle counting system provides an accurate and efficient approach to calibration. The calibration unit includes an aerosol inlet, a flow meter downstream of the aerosol inlet, and a mixer. The flow meter receives the aerosol flow from the aerosol inlet and provides an output flow to the mixer. The mixer receives the output flow from the flow meter and also has a dilution gas inlet. The mixer provides a mixer output flow for reception by the volatile particle remover or particle counter. A first flow controller controls flow into the dilution gas inlet. The calibration unit also includes a bypass inlet. A second flow controller controls flow into the bypass inlet, and a control loop controls the bypass flow such that the aerosol flow tracks a reference value.

15 Claims, 2 Drawing Sheets

CALIBRATION UNIT FOR VOLATILE PARTICLE REMOVER

BACKGROUND OF THE INVENTION

1. Field of the Invention

The invention relates to measuring solid particle number concentrations from engine or vehicle exhausts in real-time, and to a penetration and removal efficiency calibration unit for a volatile particle remover (VPR) in a solid particle counting system (SPCS).

2. Background Art

European Particle Measurement Program (PMP) proposed a draft regulation for measuring solid particle number emission in exhaust from light-duty diesel vehicles. As shown in FIG. 1, the measurement system consists of a pre-classifier 10, a hot particle diluter (PND1) 12, an evaporation unit (EU) 14, a cold particle diluter (PND2) 16, and a condensation particle counter (CPC) 18. The hot particle diluter (PND1) 12, evaporation unit (EU) 14, and cold particle diluter (PND2) 16 are referred to as the Volatile Particle Remover (VPR) 20. FIG. 1 shows a simplified schematic of the measurement system.

The VPR 20 dilutes diesel aerosol in PND1 12 and PND2 16. The EU 14 in the VPR 20 is operated at a high temperature (such as 300 to 400° C.) to evaporate volatile particles into gas phase. By following dilution from PND2 16 with room temperature dilution air, the aerosol is cooled down, and the volatile material concentration is reduced to the level to avoid the formation of the volatile particles. Thus, volatile particles are removed, and solid particles only move into the CPC 18. The concentration of the solid particles is measured in the CPC 18.

To have accurate measurement on solid particle concentration, PMP recommended that the solid particle penetration on the VPR 20 should be verified by mono-disperse solid particles at 30, 50, and 100 nm. The removal efficiency of the VPR 20 for volatile particles should be tested with mono-disperse C40 particles with 30 nm diameter. To measure penetrations for mono-disperse solid particle particles and removal efficiency for mono-disperse C40 particles on the VPR 20, mono-disperse particles need to be sent into the VPR with a CPC for the diluted concentration, and be sent into a CPC for the raw concentration. Equations 1 and 2 show the calculation for the penetration and removal efficiency:

$$P = \frac{C_{Diluted} * DR_1 * DR_2}{C_{Upstream}} \quad (1)$$

$$E_{Removal} = 1 - P \quad (2)$$

where, P is the penetration; $E_{Removal}$ is the removal efficiency for C40 particles; $C_{Diluted}$ is the diluted concentration for mono-disperse particles (solid or C40 particles), $C_{Upstream}$ is the raw (upstream) concentration for mono-disperse particles; DR1 is the dilution ratio on the PND1; and, DR2 is the dilution ratio on the PND2. While the single size aerosol is connected to point A in FIG. 1, $C_{Diluted}$ is measured. While the single size aerosol is connected to point B in FIG. 1, $C_{Upstream}$ is measured.

The Differential Mobility Analyzer (DMA) is widely used to select the single size particles. The selected single size particle concentration is extremely sensitive to the inlet flow and the outlet flow from the DMA. With small change on those flows, large variation may be detected on the raw concentration particles. From equation 1, it is observed that the raw concentration $C_{Upstream}$ is assumed no change and as the same as the measured raw concentration while the mono-disperse aerosol is sent into the VPR. Any variation on the raw concentration for the mono-disperse particle causes the error on the penetration and removal efficiency. Thus, the concentration of the mono-disperse particles should be stable and kept unchanged.

Under most of circumstances, inlet flows for the VPR and a CPC are different. The system needs to be adjusted slightly to keep the outlet flow unchanged from the DMA. This flow needs to be monitored carefully to ensure the stable and constant concentration for the mono-disperse particles. Thus, the calibration test and experimental setups for solid particle penetration and removal efficiency with mono-disperse particles are time consuming, and require that the operator have good background and knowledge with aerosol science and particle instruments. This is unrealistic in the automobile industry since few operators have background for aerosol science and related technologies.

SUMMARY OF THE INVENTION

It is an object of the invention to provide a penetration and removal efficiency calibration unit for a volatile particle remover (VPR) in a solid particle counting system (SPCS).

In preferred embodiments of the invention, the flow in the DMA is controlled as constant while flows into the VPR or CPC are varied. Thus, the stable concentration particles for mono-disperse particles may be obtained.

According to the invention, an accurate and more efficient approach is provided to calibrate the VPR in the SPCS for the penetration for single size solid particles and removal efficiency for single size volatile particles.

In one particular implementation, single size particles are selected with a Differential Mobility Analyzer (DMA). An orifice flow meter is installed downstream of the DMA. The particle losses on the orifice flow meter can be ignored. The outlet flow from the DMA is measured by the orifice flow meter in real-time.

In further detail, the aerosol flow is mixed downstream of the orifice flow meter with particle free dilution air in a mini-cyclone. The mini-cyclone mixes the aerosol with dilution air flow fast and without particle losses. In the meantime, the cyclone moves out particles larger than 2.5 µm. Thus, the cyclone protects the system from contamination.

In this implementation, a mass flow controller or a proportional valve with a PID loop controls the by-pass flow. By adjusting the by-pass flow automatically, the outlet flow from the DMA is kept as constant while flow rates into the VPR in the SPCS and the CPC are different. As a result, the concentration from the DMA is kept as constant during the test. This ensures stable concentrations for the single size particles, and more accurate results are obtained.

In one aspect of the invention, a penetration and removal efficiency calibration unit for a volatile particle remover in a solid particle counting system is provided. The calibration unit comprises an aerosol inlet, a flow meter downstream of the aerosol inlet, and a mixer. The flow meter receives the aerosol flow from the aerosol inlet and provides an output flow. The mixer receives the output flow from the flow meter, has a dilution gas inlet, and provides a mixer output flow. A first flow controller controls flow into the dilution gas inlet. The calibration unit further comprises a bypass inlet, and a second flow controller controlling flow into the bypass inlet. A control loop controls the bypass flow such that the aerosol flow tracks a reference value.

At the more detailed level, the invention comprehends additional features. For example, the reference value may be a constant flow. The mixer may take the form of a mini-cyclone. The control loop may be implemented as a proportional, integral, derivative control loop. The first flow controller may comprise a mass flow controller. The second flow controller may comprise a mass flow controller or a proportional valve.

DETAILED DESCRIPTION OF THE PREFERRED EMBODIMENT

Figure 1:
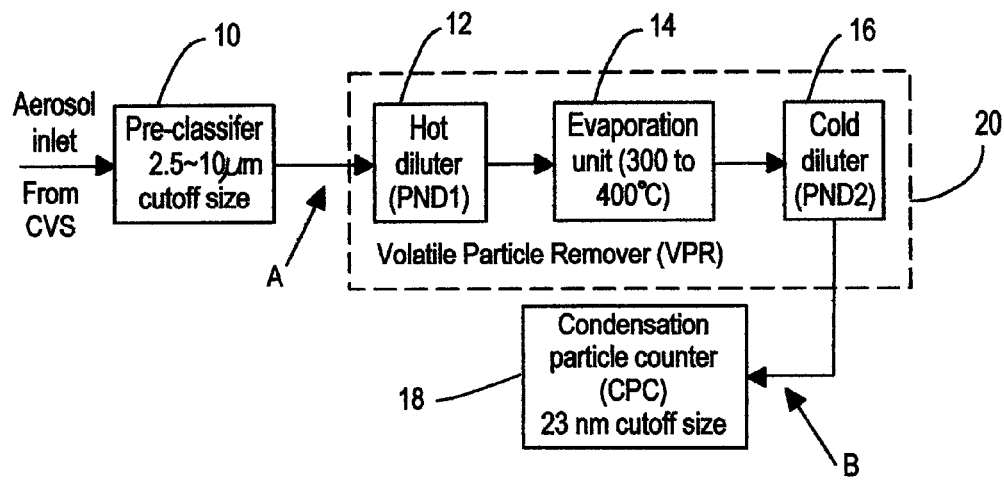
FIG. 1 illustrates a simplified schematic of an existing measurement system.
Figure 2:
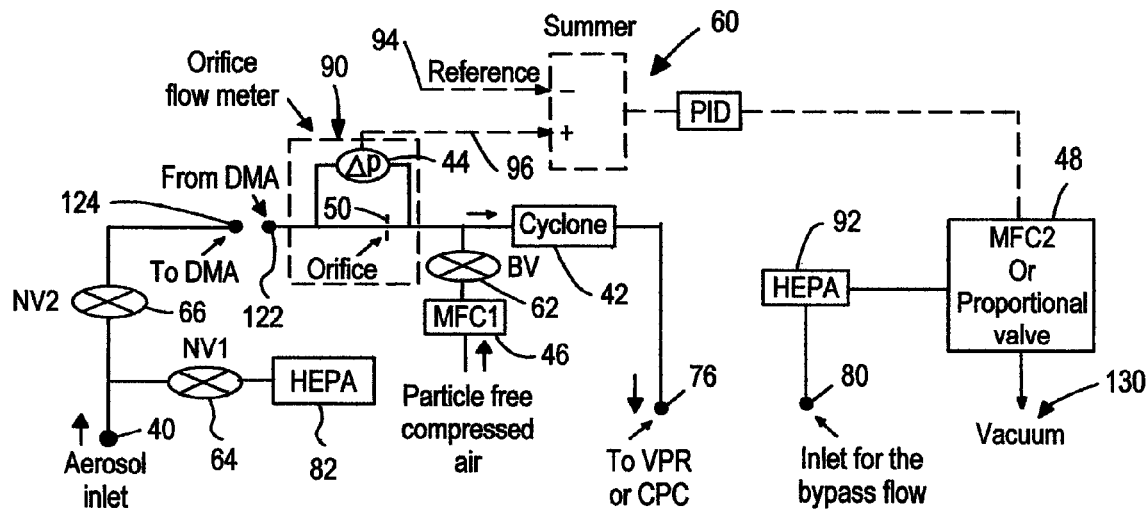
FIG. 2 illustrates a schematic for a calibration unit in a preferred embodiment of the invention.
Figure 3:
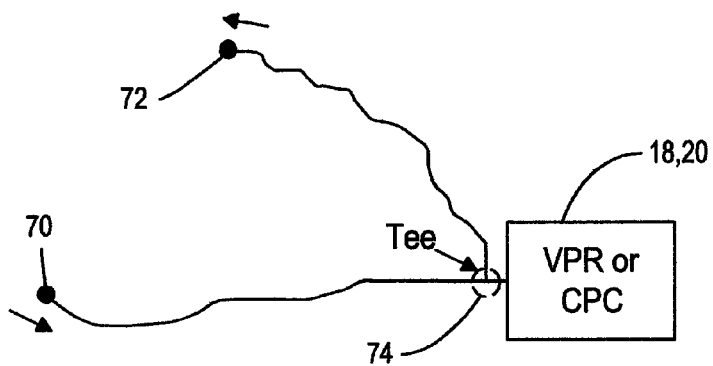
FIG. 3 illustrates the connection between the calibration unit and the inlet of the VPR or CPC.
Figure 4:
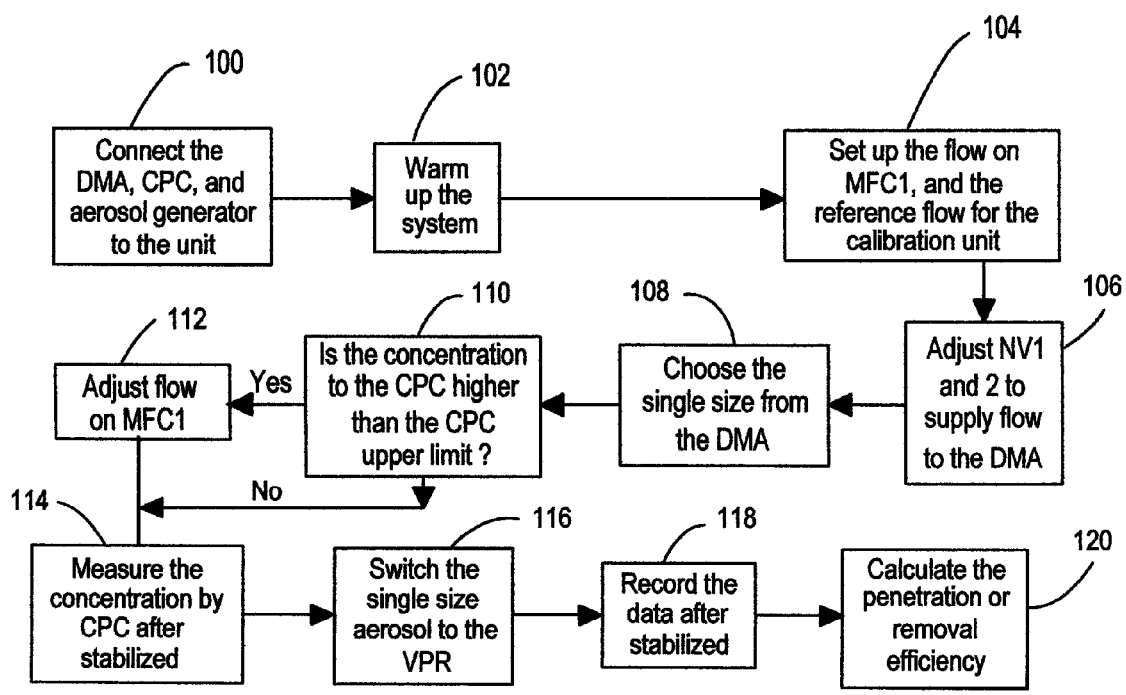
FIG. 4 illustrates the operation procedure for the calibration unit.

FIGS. 2-4 illustrate the preferred embodiment of the invention.

As best shown in FIG. 2, the calibration unit consists of aerosol inlet 40, a cyclone 42, differential pressure transducer 44, two mass flow controllers 46, 48 or a mass flow controller 46 and a proportional valve 48, an orifice 50, a PID control loop 60, a ball valve 62 and needle valves 64, 66, etc. FIG. 2 shows the schematic for the calibration unit.

Before operating the system, the system needs to be set up. The port 124 "To DMA" is connected to the inlet of a differential mobility analyzer (DMA), and the port 122 "From DMA" is connected to the outlet of the DMA. The DMA is not included in the system. To minimize particle losses, the tubing connecting the inlet and the outlet of the DMA should be as short as possible.

FIG. 3 shows the connection between the calibration unit and the inlet of the VPR 20 or CPC 18. There are three flexible tubings (from point 70 to point 74, from point 74 to point 72, and from point 74 to the inlet of the VPR 20 or CPC 18) and a Tee (at point 74) shown in FIG. 3. There are one inlet and two outlets for the Tee. The port 76 "To VPR or CPC" in FIG. 2 is connected to point 70 in FIG. 3. Point 72 in FIG. 3 is connected to port 80 "Inlet for the by-pass flow" in FIG. 2. The length of those three tubings should be minimized. The aerosol flow moves into the VPR 20 or CPC 18 through points 70, 74, and the inlet of the VPR 20 or CPC 18. The excess flow is vented through the other port of the Tee into the calibration unit.

When the raw and diluted particle concentrations are measured, the aerosol flow rate in the tubing from 70 to 74 is kept as the constant. By varying the by-pass flow in the tubing from 74 to 72, the right amount of flow moves into the VPR 20 or the CPC 18. In the meantime, the inlet and outlet flows for the DMA are kept unchanged. The tubing length from the outlet of the Tee to the inlet of the VPR 20 or CPC 18 should be as short as possible. Under most of circumstances, it is much shorter than the length from 70 to 74. Therefore, the difference of particle concentration can be ignored while the flow is different at the inlet of the VPR 20 and the CPC 18.

Poly-disperse solid particles or C40 particles are provided into the calibration unit from the port 40 of the aerosol inlet. By adjusting needle valves NV1 64 and NV2 66, the excess aerosol flow is vented into the atmosphere through NV1 64 and the HEPA 82 which is downstream of the NV1 64. Under some circumstance, the aerosol generator or C40 generator cannot provide enough flow for the DMA. The makeup air is needed, and moves into the DMA through the HEPA 82 and NV1 64. To have stable and constant concentration of single size particles, the size distribution and concentration from the aerosol generator or the C40 generator should be constant during the test. Most of commercially available particle generators can satisfy this requirement.

As mentioned above, the single size particles are selected by the DMA. Aerosol flow rate into the DMA strongly influences the concentration and the selected size for particles. If aerosol flows into and out from the DMA are fluctuated, the concentration and size will not be stable. For most of DMA operation conditions, the aerosol inlet flow is the same as the outlet of aerosol flow on the DMA. The inlet flow to the DMA is measured but there may be no output signal on the DMA. An orifice flow meter 90, which consists of differential pressure transducer 44 and flow orifice 50, is installed downstream of the DMA. The flow on the orifice flow meter 90 is calibrated with an accurate flow meter, and it is a function of the pressure difference over the orifice 50. This orifice flow meter 90 is used to measure the outlet flow from the DMA. Since the aerosol concentration downstream of the DMA is much lower than that of the upstream of the DMA, the chance for the orifice flow meter 90 getting plugged by particles is reduced by installing it downstream of the DMA. In an alternative arrangement, the flow meter could be installed upstream of the DMA.

Particle free compressed air moves into the calibration unit through mass flow controller 1 (MFC1) 46 and ball valve (BV; which can be a manual valve or air actuated valve) 62 and mixes with aerosol from the DMA in the mini-cyclone 42 downstream of the orifice flow meter 90. The flow rate for the dilution air is controlled by MFC1 46. The flow on the MFC1 46 is set based on the inlet flow of the VPR 20 or CPC 18 and the concentration of the single size particles. Equations 3 and 4 show flow balance in the system while the calibration unit is connected to the inlet of the VPR 20 and the inlet of the CPC 18, respectively:

$$Q_{total} = Q_{DMA} + Q_{MFC1} = Q_{VPR} + Q_{by\text{-}pass} \quad (3)$$

$$Q_{total} = Q_{DMA} + Q_{MFC1} = Q_{CPC} + Q_{by\text{-}pass} \quad (4)$$

where, $Q_{DMA}$ is the outlet flow from DMA; $Q_{MFC1}$ is the particle free air flow controlled by MFC1 46; $Q_{total}$ is the flow for the mixture of $Q_{DMA}$ and $Q_{MFC1}$; $Q_{VPR}$ is the inlet flow to the VPR 20; $Q_{CPC}$ is the inlet flow rate to the CPC 18; and, $Q_{by\text{-}pass}$ is the by-pass flow controlled by MFC2 or a proportional valve 48. During the whole test, $Q_{total}$ is kept as constant while $Q_{VPR}$ and $Q_{CPC}$ are changed. Thus, by varying $Q_{by\text{-}pass}$, the total flow stays unchanged.

The flow on MFC1 46 is controlled based on the outlet flow from the DMA, the inlet flows to the VPR 20 and the CPC 18, and the concentration of the mono-disperse particles. If the outlet flow on the DMA is larger than inlet flows on the VPR 20 and the CPC 18, and the particle concentration (raw) from the DMA is lower than the upper limit of the CPC 18, the flow rate on MFC1 46 can be set at zero. Thus, no dilution air flow moves into the system through MFC1 46. To avoid leak on the MFC1 46 to change particle concentrations, the ball valve 62 (BV) can be closed manually or automatically. If the concentration from the DMA is higher than the upper limit of the CPC 18 or a lower concentration is desired, the aerosol can be diluted to the desired concentration by adding dilution air flow from the MFC1 46.

While one or both of flows for the VPR 20 inlet and CPC 18 inlet are larger than the outlet flow of the DMA, the flow on MFC1 46 can be set to a value which the sum ($Q_{total}$) of $Q_{DMA}$ and $Q_{MFC1}$ is larger than the bigger flow between the inlet of the VPR 20 and the inlet of the CPC 18. In the meantime, the concentration of the raw aerosol is at the desired and lower than the upper limit on the CPC 18. Once the flow is set on MFC1 46 and the desired concentration is obtained, the flow is kept constant during the test. Thus, $Q_{total}$ is constant in the whole test.

The outlet flow from port 76 "To VPR or CPC" flows into the VPR 20 or CPC 18 through points 70 and 74 in FIG. 3 into the inlet of the VPR 20 or the CPC 18. To ensure that the outlet flow from the DMA is constant during the test, the by-pass flow from point 74 to 72 into the calibration unit is controlled by mass flow controller 2 (MFC2) or a proportional valve 48. A vacuum source 90 draws the by-pass flow into MFC2 or a proportional valve 48. The by-pass flow moves through a HEPA filter 92 before it moves into the MFC2 or the proportional valve 48. The HEPA 92 protects the MFC2 or the proportional valve 48 from contamination by particles.

A proportional, integral, and derivative loop (PID) 60 is used to control MFC2 or the proportional valve 48. The reference flow 94 which is the desired flow rate for the DMA outlet flow is the set point. The flow measured by the orifice flow meter 90 is as the input for the PID loop 60. By comparing the difference between the reference value 94 and the measured value 96 in the PID loop 60, MFC2 or the proportional valve 48 is adjusted to maintain the outlet flow on the DMA as a constant. As a result, the flow on the DMA can be kept as constant during the whole test.

While the aerosol is connected to the CPC 18, the raw (upstream) concentration is measured. By adjusting the bypass flow automatically, the flow from the DMA is kept as constant. The variation of the single size particle concentration is minimized. After the concentration is stabilized, the data can be recorded manually or automatically. The diluted concentration downstream of the VPR 20 in the SPCS is measured by sending the aerosol into the VPR 20 in the SPCS. By adjusting the by-pass flow automatically with MFC2 or the proportional valve 48, the outlet flow on the DMA is the same as that for the flow into the CPC 18. As a result, the concentration for the single size particle is not changed during the aerosol into either the VPR 20 or the CPC 18.

FIG. 4 summarizes the operation procedure for the calibration unit. At block 100, the Differential Mobility Analyzer (DMA), particle counter (CPC), and aerosol generator are connected to the calibration unit. At block 102, the system is warmed up. At block 104, the flow for the particle free compressed air on MFC1 (46, FIG. 2) is set and the reference flow (94, FIG. 2) is set. At block 106, The needle valves (64, 66, FIG. 2) are adjusted to supply the needed flow for the DMA. At block 108, the single size for the particles from the DMA is selected. At block 110, if the particle concentration provided to the CPC is higher than the CPC's upper limit, the flow at MFC1 is adjusted as indicated at block 112. Flow proceeds to block 114, and after the system stabilizes, concentration is measured at the CPC. At block 116, the single size aerosol is provided to the VPR, and at block 118, data is recorded after the system stabilizes. Finally, at block 120, penetration and/or removal efficiency are calculated.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A penetration and removal efficiency calibration unit for a volatile particle (VPR) or a calibration unit for a condensation particle counter (CPC), the calibration unit comprising:
   a flow meter measuring a flow rate from a differential mobility analyzer and providing an output flow;
   a mixer receiving the output flow from the flow meter and receiving a flow of particle free dilution gas, the mixer providing a mixer output flow, wherein a portion of the mixer output flow is provided to the VPR or CPC;
   a first flow controller for controlling the flow of particle free dilution gas to the mixer;
   a bypass inlet receiving a bypass flow, the bypass flow being the remainder of the mixer output flow that bypasses the VPR or CPC;
   a second flow controller receiving the bypass flow from the bypass inlet, for controlling the bypass flow;
   a vacuum source drawing the bypass flow into the second flow controller; and
   a control loop controlling the bypass flow such that the aerosol flow from the differential mobility analyzer tracks a reference value as the flow into the VPR or CPC varies.

2. The calibration unit of claim 1 wherein the reference value is a constant flow.

3. The calibration unit of claim 1 wherein the mixer comprises a mini-cyclone.

4. The calibration unit of claim 1 wherein the control loop comprises a proportional, integral, derivative control loop.

5. The calibration unit of claim 1 wherein the first flow controller comprises a mass flow controller.

6. The calibration unit of claim 1 wherein the second flow controller comprises a mass flow controller.

7. The calibration unit of claim 1 wherein the second flow controller comprises a proportional valve.

8. A penetration and removal efficiency calibration unit for a volatile particle remover (VPR) or a calibration unit for a condensation particle counter (CPC), the calibration unit comprising: an aerosol inlet; a flow meter downstream of the aerosol inlet, the flow meter receiving the aerosol flow from the aerosol inlet and providing an output flow; a mixer receiving the output flow from the flow meter and having a dilution gas inlet, the mixer providing a mixer output flow, wherein a portion of the mixer output flow is provided to the VPR or CPC; a first flow controller for controlling flow into the dilution gas inlet; a bypass inlet receiving a bypass flow that is a remainder of the mixer outlet flow that bypasses the VPR or CPC; a second flow controller in flow communication with the bypass inlet to receive the bypass flow from the bypass inlet, for controlling flow into the bypass inlet; and a control loop controlling the bypass flow such that the aerosol flow tracks a reference value.

9. The calibration unit of claim 8 wherein the reference value is a constant flow.

10. The calibration unit of claim 8 wherein the mixer comprises a mini-cyclone.

11. The calibration unit of claim 8 wherein the control loop comprises a proportional, integral, derivative control loop.

12. The calibration unit of claim 8 wherein the first flow controller comprises a mass flow controller.

13. The calibration unit of claim 8 wherein the second flow controller comprises a mass flow controller.

14. The calibration unit of claim 8 wherein the second flow controller comprises a proportional valve.

15. A penetration and removal efficiency calibration unit for a volatile particle remover (VPR) or a calibration unit for a condensation particle counter (CPC), the calibration unit comprising:
- an aerosol inlet;
- a differential mobility analyzer (DMA) receiving aerosol from the aerosol inlet, for classifying particles;
- a vent between the aerosol inlet and the DMA for venting excess aerosol flow, or for providing make-up air to the DMA;
- a flow meter measuring a flow rate from the differential mobility analyzer and providing an output flow;
- a mixer receiving the output flow from the flow meter and receiving a flow of particle free dilution gas, the mixer providing a mixer output flow, wherein a portion of the mixer output flow is provided to the VPR or CPC;
- a first flow controller for controlling the flow of particle free dilution gas to the mixer;
- a bypass inlet receiving a bypass flow, the bypass flow being the remainder of the mixer output flow that bypasses the VPR or CPC;
- a second flow controller for controlling the bypass flow; and
- a control loop controlling the bypass flow such that the aerosol flow from the differential mobility analyzer tracks a reference value as the flow into the VPR or CPC varies.

* * * * *